United States Patent
Fonfe et al.

(10) Patent No.: US 10,494,331 B2
(45) Date of Patent: Dec. 3, 2019

(54) PROCESS FOR OPERATING A PLANT FOR PREPARING AN ALKANESULFONIC ACID

(71) Applicant: Evonik Degussa GmbH, Essen (DE)

(72) Inventors: Benjamin Fonfe, Frankfurt (DE); Chiu Kee Cheung, Alzenau (DE); Ali Hartwig, Gruendau (DE); Nadine Duerr, Mobile, AL (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/129,375

(22) Filed: Sep. 12, 2018

(65) Prior Publication Data

US 2019/0077748 A1 Mar. 14, 2019

(30) Foreign Application Priority Data

Sep. 13, 2017 (EP) ..................................... 17190801

(51) Int. Cl.
*C07C 303/16* (2006.01)
(52) U.S. Cl.
CPC .................. *C07C 303/16* (2013.01)
(58) Field of Classification Search
CPC ..................................................... C07C 303/16
See application file for complete search history.

(56) References Cited

U.S. PATENT DOCUMENTS

| 2,727,920 A | 12/1955 | Johnson et al. |
| 6,531,629 B1 | 3/2003 | Eiermann et al. |

FOREIGN PATENT DOCUMENTS

| WO | WO 00/31027 A1 | 6/2000 |

OTHER PUBLICATIONS

Extended European Search Report dated Mar. 8, 2018 in Patent Application No. 17190801.5, 9 pages.
U.S. Pat. No. 10,023,531, Jul. 17, 2018, US 2016-0304446 A1, Fonfe, et al.
U.S. Pat. No. 10,052,620, Aug. 21, 2018, US 2018-0133704 A1, He, et al.
U.S. Appl. No. 15/778,802, filed May 24, 2018, Fonfe, et al.
U.S. Appl. No. 16/121,979, filed Sep. 5, 2018, Fonfe, et al.
U.S. Appl. No. 16/129,375, filed Sep. 12, 2018, Fonfe, et al.

*Primary Examiner* — Sikarl A Witherspoon
(74) *Attorney, Agent, or Firm* — Oblon, McClelland, Maier & Neustadt, L.L.P.

(57) ABSTRACT

The present invention relates to a process for operating a plant for preparing an alkanesulfonic acid, wherein said alkanesulfonic acid is prepared by oxidation of an alkylmercaptan, dialkydisulfide and/or dialkylpolysulfide and the one or more alkyl radicals of the alkylmercaptan, dialkydisulfide and/or dialkylpolysulfide are identical with the alkyl radical of the alkylsulfonic acid to be prepared, characterized in that the oxidation is performed in the presence of an at least stoichiometric amount of an oxoacid of nitrogen, e.g. nitric acid, relative to the amount of said alkylmercaptan, dialkyldisulfide and/or dialkylpolysulfide during the start-up phase of the plant of the plant, wherein the start up phase comprises the steps adding an oxoacid of nitrogen to the reactor, adding sulfur-containing reactant progressively so that it is converted to alkanesulfonic acid, filling up the compile volume of the reactor by adding progressively sulfur-containing reactant and if needed oxoacid of nitrogen to make sure that it is in excess, once the reactor is full, transitioning out of the start-up phase by adding an oxygen containing fluid, and during the running phase, keeping the reaction volume full by balancing the volume of product withdrawn with the volume of sulfur-containing reactant added.

8 Claims, No Drawings

PROCESS FOR OPERATING A PLANT FOR PREPARING AN ALKANESULFONIC ACID

This application is based upon and claims the benefit of priority to European Application No. 17190801.5, which was filed on Sep. 13, 2017.

The present invention relates to a process for operating a plant for preparing an alkanesulfonic acid during the start-up phase of said plant and to the use of an oxoacid of nitrogen, e.g. nitric acid, containing liquid phase as matrix into which the reactants are fed in during the start-up phase of a plant for preparing an alkanesulfonic acid.

Sulfonic acids are the organic derivatives of sulfuric acid, from which they differ structurally in the replacement of a hydroxyl group with an organic radical. The general structural formula of the sulfonic acids therefore is R—$SO_3$—H, where R denotes an organic radical, such as a saturated or an olefinic alkyl, an aryl or heteroaryl for example. Depending on this organic radical, a distinction is made between aliphatic, aromatic and heteroaromatic sulfonic acids. The free sulfonic acids are generally colourless and hygroscopic substances whose acid strength corresponds to that of the inorganic acids. Indeed, with a $pK_a$ of −5.5, trifluoromethanesulfonic acid is one of the strongest known acids and therefore belongs to the group known as the superacids. In contrast to the sulfate salts of mercury, lead and silver, the corresponding sulfonates have very good solubility in water.

The commercially most relevant sulfonic acids are the alkanesulfonic acid. The simplest representative of the alkanesulfonic acids is methanesulfonic acid, which is commonly also abbreviated to MSA. At the same time, by virtue of its diverse possibilities of use, methanesulfonic acid is also the most economically important alkanesulfonic acid. For example, methanesulfonic acid serves as a solvent and catalyst for a variety of organic reactions, such as alkylations, esterifications, polymerizations or heterocycle syntheses, for example. Another field of application is the formation of acid addition salts of basic pharmaceuticals with methanesulfonic acid in human medicine. In addition, methanesulfonic acid is increasingly finding use as a constituent of cleaning products, since the absence of colour and odor in this acid allows the easy integration of methanesulfonic acid into cleaning solutions. From an industrial standpoint, the most significant are the metal salts of methanesulfonic acid, which find use as electrolytes in methanesulfonic acid electroplating baths, especially in the production of printed circuit boards for the electronics industry. Oil drilling is another field of application for methanesulfonic acid: the oil-bearing rock strata accessed by boreholes often release the oil only to a limited extent or even not at all. For enhanced release of the oil, therefore, the oil-containing rock strata are softened using methanesulfonic acid.

On an industrial scale, alkanesulfonic acids are typically prepared by oxidizing alkylmercaptans, dialkyldisulfides and/or dialkylpolysulfides. When the preparation of alkanesulfonic acids starts from alkylmercaptans, said mercaptan is first oxidized to a dialkyldisulfide and/or a dialkylpolysulfide, which in the following is subjected to a further oxidation to yield the alkanesulfonic acid. Typical oxidizing agents are nitric acid, oxygen, and hydrogen peroxide or chlorine. Besides nitric acid, other oxoacids of nitrogen can also be used either as the sole oxidizing agent or in combination with oxygen. For example, U.S. Pat. No. 2,727,920 A discloses a process for the preparation of alkanesulfonic acids from their corresponding mercaptan or disulfide comprising an oxidation step in an excess of aqueous solution of nitric acid containing absorbed free oxygen. After the reaction, the nitric acid solution is sent to an oxygen absorber column and recycled to the oxidation reactor. The U.S. Pat. No. 6,531,629 B1 discloses a process for the preparation of alkanesulfonic acids from their corresponding mercaptans, dialkyldisulfides and/or dialkylpolysulfides by oxidation with an excess of nitric acid. The nitric acid is separated from the alkanesulfonic acid in a vacuum rectification column and condensed to give a liquefied nitric acid condesate. The $NO_x$-containing offgas streams from the oxidation are passed to a plate column for the regeneration of nitric acid. The nitric acid condensate is also passed to the plate column for the regeneration of nitric acid.

Despite the corrosive effect of alkanesulfonic acids on metals or alloys, the preparation of alkanesulfonic acids on the industrial scale is typically performed in chemical reactors made, of suitable alloys. The reasons for this are that materials other than metals or alloys such as plastics or glass either have not proven to be corrosion resistant or practicable for the industrial scale. A further reason is that suitable alloys such as those conforming to the DIN material numbers 1.4571 and 1,4539 are only weakly attacked by alkanesulfonic acids at temperatures below 70° C.

However, it was found that the corrosion of such alloys is significantly increased by the additional presence of non-oxidized sulfur containing compounds or not completely oxidized sulfur containing compounds, such as dialkyldisulfides, for example dimethyldisulfide (DMDS), or the additional presence of intermediates, which occur in the preparation of alkanesulfonic acids by oxidation of alkylmercaptans, dialkyldisulfides, and/or dialkylpolysulfides such as an S-alkyl alkanethiosulfonate, for example S-methyl methanethiosulfonate (MMTS). For example, an alloy conforming to the DIN material number 1,4571 is subject to corrosion rates, measured as loss of material thickness, of more than 40 mm per year (min/a) when it is in contact with methanesulfonic acid in the presence of dimethyldisulfide or S-methyl methanethiosulfonate. However, a loss of material thickness of 10 mm per year or more is already considered as problematic with respect to the durability and in particular the pressure resistance of a chemical reactor. By comparison, corrosion rates in the low single digit range of ca. 2 mm per year (mm/a) are observed when the same alloy is contacted with methanesulfonic acid, however in the absence of dimethyldisulfide or S-methyl methanethiosulfonate. Without wishing to be bound to a specific theory, it is believed that the corrosion of alloys is initiated by alkanesulfonic acids and that said corrosion is accelerated in the presence of a sulfur containing compound, where the sulfur atoms have free valence electrons, such as a dialkyldisulfide or S-alkyl alkanethiosulfonate. It is further believed that the metal ions, which are dissolved from the alloys through the action of the alkanesulfonic acid on said alloy are coordinated by the not fully oxidized sulfur containing compounds, such as dialkyldisulfide or S-alkyl alkanethiosulfonate. Typically, the thus formed complexes would be in an equilibrium with the alloy surface to the effect that no accelerated corrosion phenomena would be observed. However, the said equilibrium appears to be disturbed in the presence of not fully oxidized sulfur containing compounds. It is believed that due to their ionic nature the complexes precipitate from the liquid medium, which mainly consists of the aprotic dialkyldisulfide or S-alkyl alkanethiosulfonate, and thus they are withdrawn from the equilibrium. Said withdrawal of the metal complexes is considered the main reason for the increased corrosion phenomena mentioned above.

Said increased corrosion is a major problem during the start-up phase of a plant for preparing alkanesulfonic acids, where the concentration of dialkyldisulfides and/or reaction intermediates such as S-alkyl alkanethiosulfonate is at its highest. Corrosion phenomena do not only impair the purity and quality of the produced alkanesulfonic acid. More importantly, they also lead to severe damage to the production plant, which inevitably results in a plant standstill and further, in a high loss of sales and high repair costs.

Thus, there is a need for a process for operating a plant for preparing alkanesulfonic acids, which avoids the aforementioned problems.

It was found that this problem is solved when the oxidation of an alkylmercaptan, dialkyldisulfide and/or dialkylpolysulfide to the corresponding alkanesulfonic acid is performed in the presence of an at least stoichiometric amount of an oxoacid of nitrogen, e.g. nitric acid, relative to the amount of said alkylmercaptan, dialkyldisulfide and/or dialkylpolysulfide during the start-up phase of the plant. The presence of an at least stoichiometric amount of an oxoacid of nitrogen, e.g. nitric acid, leads to a rapid and complete oxidation of the sulfur containing starting materials. Thus, operation conditions are avoided in which a corrosive alkanesulfonic acid and large amounts of a corrosion promoting dialkyldisulfide or S-alkyl alkanesulfonic acid are simultaneously present in the reactor of said plant. An additional benefit of the use of stoichiometric amounts of an oxoacid of nitrogen, e.g. nitric acid, in the start-up phase is that it inhibits the corrosion of the alloy of those parts of the plant, which are in contact with the reaction mixture, due to its passivating effect on metals and alloys. In the next step the sulfur-containing compound to be oxidized is fed into the provided oxoacid of nitrogen to give a product mixture containing the desired oxidation product, and this step is repeated until the available inner volume of the reactor is filled completely with the product mixture and if required, oxoacid of nitrogen is added to make sure that the reaction proceeds. Once the reactor is full, the process transition out of the start-up phase to by adding an oxygen containing fluid. During this phase of the process, the reactor volume is kept full by balancing the volume of product mixture withdrawn from the reactor with the volume of the sulfur-containing reactant added.

Object of the present invention is therefore a process for operating a plant for preparing an alkanesulfonic acid, wherein said alkanesulfonic acid is prepared by oxidation of an alkylmercaptan, dialkydisulfide and/or dialkylpolysulfide, characterized in that the oxidation is performed in the presence of an at least stoichiometric amount of an oxoacid of nitrogen, e.g. nitric acid, relative to the amount of said alkylmercaptan, dialkyldisulfide and/or dialkylpolysulfide during the start-up phase of the plant, comprising the steps
i) providing an oxoacid of nitrogen in a reactor,
ii) feeding an alkylmercaptan, dialkydisulfide and/or dialkylpolysulfide containing stream into the oxoacid of nitrogen of step i) to give an alkanesulfonic acid containing product mixture, and
iii) repeating step ii) until the available inner volume of the reactor is filed completely with the alkanesulfonic acid containing product mixture obtained in step ii),
iv) feeding additional oxoacid of nitrogen into the reactor, when the amount of oxoacid of nitrogen provided in step i) is not enough to fill the available inner volume of the reactor with the product mixture obtained in step ii).
v) feeding an oxygen containing fluid stream into the reactor, when the available inner volume of the reactor is completely filled with the product mixture obtained in the step and/or in the step iii),
vi) removing at least part of the alkanesulfonic acid containing product mixture from the reactor, and
vii) feeding an alkylmercaptan, dialkyldisulfide and/or dialkylpolysulfide containing stream into the reactor to yield a reaction mixture, wherein said alkylmercaptan, dialkyldisulfide and/or dialkylpolysulfide is identical with the alkylmercaptan, dialkyldisulfide and/or dialkylpolysulfide of any of the preceding steps, wherein the volume of the alkylmercaptan, dialkyldisulfide and/or dialkylpolysulfide containing stream, fed into the reactor in step vii), equals the volume of the product mixture removed from the reactor in step vi).

In the context of the present invention, the term oxoacid of nitrogen is used according to the general knowledge of the person skilled in the art and refers to all types of acids, which contain hydrogen, oxygen, and nitrogen, with at least one hydrogen atom bond to oxygen that can dissociate to produce the $H^+$ cation and anion of the acid. There are mononitrogen oxoacids of the general formula $HNO_n$ with n being, an integer from 1 to 4 and $H_3NO_n$ with n=1 or 2 as well as dinitrogen oxoacids of the general formula $H_2N_2O_n$ with n=2 or 3. Representatives of the mononitrogen oxoacids of the general formula $HNO_n$ are hyponitrous acid (HNO), which also occurs in the form of the dinitrogen oxoacid of the formula $H_2N_2O_2$, nitrous acid ($HNO_2$), nitric acid ($HNO_3$), and peroxynitric acid ($HNO_4$). A representative of the mononitrogen oxoacids of the general formula $H_3NO_n$ is hydroxylamine ($H_3NO$). A representative of dinitrogen oxoacids of the general formula $H_2N_2O_n$ is the aforementioned hyponitrous acid ($H_2N_2O_2$). Since oxoacids of nitrogen are not always used in pure form or are diluted during the course of the process of the present invention, the term oxoacid of nitrogen also refers to solutions of oxoacids of nitrogen, such as aqueous solutions of oxoacids of nitrogen, in which the oxoacid is present in dissociated form.

In the context of the present invention, the term stoichiometric amount of an oxoacid of nitrogen, e.g. nitric acid, refers to the amount of oxoacid of nitrogen, e.g. nitric acid, which is required to oxidize an alkylmercaptan, a dialkyldisulfide or a dialkylpolysulfide completely to the corresponding alkanesulfonic acid. It is common knowledge of the person skilled in the art to determine said stoichiometric amount of oxoacid of nitrogen by means of the reaction equation(s) for the oxidation of the sulfur containing starting compound with the oxoacid of nitrogen in question to the alkanesulfonic acid. For example, the oxidation of a dialkyldisulfide by nitric acid to the corresponding alkanesulfonic acid can be expressed through the reaction equation:

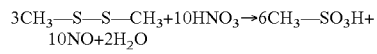
$3CH_3-S-S-CH_3+10HNO_3 \rightarrow 6CH_3-SO_3H+10NO+2H_2O$

Analogously, the oxidation of a dialkyldisulfide by nitrous acid to the corresponding alkanesulfonic acid can be expressed through the reaction equation:

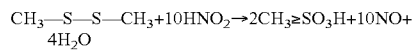
$CH_3-S-S-CH_3+10HNO_2 \rightarrow 2CH_3 \geq SO_3H+10NO+4H_2O$

Without wishing to be bound to a specific theory, it is believed that the oxidation of a dialkylpolysulfide by nitric acid or nitrous acid to the corresponding alkanesulfonic acid can be described in principle by the same or an at least similar reaction equation.

When the starting material is an alkylmercaptan, the reaction is preceded by the oxidation to the alkylmercaptan by nitric acid to give the dialkyldisulfide which is to be further oxidized to give the alkanesulfonic acid. This further oxidation step is expressed through the following reaction equation:

$$6CH_3-SH+2HNO_3 \rightarrow 3CH_3-S-S-CH_3+2NO+4H_2O$$

Analogously, the oxidation of an alkylmercaptan by nitrous acid to give the dialkyldisulfide can be expressed through the reaction equation:

$$2CH_3-SH+2HNO_2 \rightarrow CH_3-S-S-CH_3+2NO+2H_2O$$

The overall oxidation of an alkylmercaptan by nitric acid or nitrous acid to the corresponding alkanesulfonic acid can be described by the following reaction equations:

$$2H_3C-SH+4HNO_3 \rightarrow 2H_3C-SO_3H+4NO+2H_2O$$

$$2H_3C-SH+12HNO_2 \rightarrow 2H_3C-SO_3H+12NO+6H_2O$$

Hence, a molar ratio of nitric acid to alkylmercaptan of at least 2:1 (mol/mol) or a molar ratio of nitrous acid to alkylmercaptan of at least 6:1 (mol/mol) is required to completely oxidize one equivalent of an alkylmercaptan to one equivalent of the corresponding alkanesulfonic acid. In this, reaction one sulfur atom in one equivalent of the alkylmercaptan is oxidized from the oxidation state −2 to the oxidation state +4 in one equivalent of the corresponding alkanesulfonic acid. If the starting material is a dialkyldisulfide, a molar ratio of nitric acid to dialkyldisulfide of 10:3 (mol/mol) or a molar ratio of nitrous acid to dialkyldisulfide of 10:1 (mol/mol) is required to completely oxidize one equivalent of a dialkyldisulfide to two equivalents of the corresponding alkanesulfonic acid. In this reaction two sulfur atoms in one equivalent of the dialkyldisulfide are oxidized from the oxidation state −2 to the oxidation state +4 in the corresponding alkanesulfonic acid.

When different sulfur containing starting compounds are oxidized in the process according to the present invention, i.e. an alkylmercaptan and a dialkyldisulfide or an alkylmercaptan and a dialkylpolysulfide, the required amount of nitric acid depends on the ratio of the two different sulfur containing starting compounds to one another. In that case the term stoichiometric amount of nitric acid denotes the amount of nitric acid which is necessary for a complete oxidation of all starting compounds to the corresponding alkanesulfonic acid.

When an alkylmercaptan is the starting compound for the preparation of an alkanesulfonic acid in the process according to the present invention, the term "an at least stoichiometric amount of nitric acid and/or nitrous acid relative to the amount of alkylmercaptan" is used to denote a molar ratio of nitric acid to alkylmercaptan of at least 2:1 (mol/mol) and a molar ratio of nitrous acid to alkylmercaptan of at least 6:1 (mol/mol).

When a dialkyldisulfide and/or a dialkylpolysulfide is the starting compound for the preparation of an alkanesulfonic acid in the process according to the present invention, the term "an at least stoichiometric amount of nitric acid and/or nitrous acid relative to the amount of dialkyldisulfide and/or a dialkylpolysulfide" is used to denote a molar ratio of nitric acid to the alkylmercaptan of at least 10:3 (mol/mol) and a molar ratio of nitrous acid to the alkylmercaptan of at least 10:1 (mol/mol).

When a mixture of an alkylmercaptan and a dialkyldisulfide or a mixture of an alkylmercaptan and a dialkylpolysulfide or a mixture of an alkylmercaptan, dialkyldisulfide and a dialkylpolysulfide are used as the starting compound in the process according to the present invention, the term "an at least stoichiometric amount of nitric acid and/or nitrous acid relative to the amount of alkylmercaptan, dialkyldisulfide and/or dialkylpolysulfide" is used to denote a molar ratio of nitric acid to the sulfur containing starting compounds of at least 10:3 (mol/mol) and a molar ratio of nitrous acid to the sulfur containing starting compound of at least 10:1 (mol/mol).

Independent from a specific sulfur containing starting compound, the term "an at least stoichiometric amount of nitric acid and/or nitrous acid relative to the amount of alkylmercaptan, dialkyldisulfide and/or dialkylpolysulfide" is used in the context of the present invention to denote a molar ratio of nitric acid to the sulfur atom in any of the aforementioned compounds to be oxidized of at least 2:1 (mol/mol) and a molar ratio of nitrous acid to the sulfur atom in any of the aforementioned compounds to be oxidized of at least 6:1 (mol/mol).

According to the present invention the alkanesulfonic acid is prepared by oxidation of an alkylmercaptan, dialkyldisulfide and/or dialkylpolysulfide. Preferably, a dialkylpolysulfide has from 3 to 9 sulfur atoms. For simplicity, said alkylmercaptans, dialkyldisulfides and dialkylpolysulfides in their entirety are also referred to as sulfur containing starting compounds hereinafter.

The one or more sulfur atoms in said sulfur containing starting compounds are oxidized, while the alkyl groups are not subject to any oxidation and thus behave inert. Since only the sulfur atoms of the alkylmercaptan, dialkydisulfide and/or dialkylpolysulfide are oxidized, the one or more alkyl radicals of the alkylmercaptan, dialkydisulfide and/or dialkylpolysulfide are identical with the alkyl radical of the alkylsulfonic acid to be prepared. Thus, the oxidation of an alkylmercaptan, dialkyldisulfide and/or dialkylpolysulfide in the process according to the present invention always gives the corresponding alkanesulfonic acid. When the alkanesulfonic acid is prepared by oxidization of a dialkyldisulfide and/or dialkylpolysulfide, the alkyl radicals of said dialkyldisulfide and/or dialkylpolysulfide are identical and thus, a symmetrical dialkyldisulfide and/or dialkylpolysulfide is used in order to provide for a uniform reaction product. Alkylmercaptans, dialkyldisulfides and dialkylpolysulfides can be prepared according to standard procedures in the literature, which are known to the person skilled in the art of organic chemistry and thus no further explanation is needed in this respect. According to the literature, the oxidation of a dialkyldisulfide to an alkanesulfonic acid proceeds via the intermediates of an S-alkylthioalkane sulfoxide R—S—SO—R, followed by an S-alkyl alkanethiosulfonate or alkanesulfonic acid S-alkyl ester R—S—SO$_2$—R, an S-alkyl sulfoxide alkanethiosulfonate R—SO—SO$_2$—R, and a dialkyldisulfone R—SO$_2$—SO$_2$—R, with the latter being finally hydrolyzed to yield the desired alkanesulfonic acid. Said hydrolysis is effected by the quantity of water contained in the nitric acid solution used in the oxidation reaction and/or by the water which is added to the oxidation reaction. When the preparation of an alkanesulfonic starts from an alkylmercaptan, the oxidation of said alkylmercaptan yields a dialkyldisulfide at first, which is subsequently further oxidized to yield the alkanesulfonic acid, wherein the aforementioned intermediate stages are passed. Preferably, the alkyl radical of the sulfur containing starting compound is methyl, ethyl, n-propyl, iso-propyl, n-butyl, iso-butyl or tert-butyl, with methyl being particularly preferred.

Preferred oxoacids of nitrogen are nitric acid and nitrous acid. Particularly preferred is the use of nitric acid. Nitric acid and/or nitrous acid can each be used in any commercially available form. For example, the nitric acid can be used either as pure nitric acid or in diluted form as a solution, which is hereinafter also referred to as nitric acid containing liquid phase. A typical solution of nitric acid is an aqueous solution. Thus, the nitric acid can be provided in the form of an aqueous solution with a concentration of nitric acid ranging from ca. 10 to ca. 90 weight-%, in principle, it is also possible to use nitric acid in pure form with a concentration of more than 90% nitric acid, which in addition also contains, nitrogen dioxide dissolved therein, which is also known as fuming nitric acid. However, nitric add with a concentration of at least 70 weight-% can ignite highly flammable substances. For this reason, nitric acid with a concentration of 70 weight-% or more is considered to support combustions. Therefore, it is preferred to use an aqueous solution of nitric acid with a concentration of less than 70 weight-% in the process according to the present invention. Besides the safety aspect, it is a further advantage of using an aqueous nitric add solution that said solution already introduces a certain amount of water into the system. Said water is required for the final hydrolysis of the dialkyldisulfone to give the desired alkanesulfonic acid. In this case, it is therefore not required to feed additional water into the reactor. This has the advantage that it is not necessary to remove the unused part of the added water from the product mixture or at least the amount of the water to be removed is significantly lower. This makes the purification of the alkanesulfonic containing reaction mixture in a following purification, for example by distillation, less complicated and energy intensive. Preference is therefore given to the use of an aqueous solution of nitric acid or a nitric acid containing aqueous phase.

According to the present invention the oxidation of an alkylmercaptan, dialkyldisulfide and/or dialkylpolysulfide to the corresponding alkanesulfonic acid is performed in the presence of an at least stoichiometric amount of an oxoacid of nitrogen, e.g. nitric acid, relative to the amount of said alkylmercaptan, dialkyldisulfide and/or dialkylpolysulfide during the start-up phase of the plant for said process. When the oxoacid of nitrogen, e.g. nitric acid and/or nitrous acid, is consumed during the oxidation reaction, it is converted to a nitrogen oxide $NO_x$, i.e. NO and/or $NO_2$. The thus formed nitrogen oxide(s) can accumulate in the reactor, which can further lead to a back-pressure in the reactor with respect to the oxoacid of nitrogen. e.g. nitric acid, and/or the sulfur containing starting materials, which are to be fed into the reactor. The higher the amount of the nitrogen oxides in the reactor, the higher the respective hack-pressure in the reactor. In order to avoid the accumulation of nitrogen oxides in the reactor and the formation of an increasing back-pressure it is therefore preferred that the process according to the present invention is performed in a reactor system, which is equipped with an exhaust valve, in the context of the present invention the exhaust valve is designed such that it only allows the escape of the nitrogen oxides from the reactor but not the inflow of air from the outside into the reactor; i.e. the reactor is fitted with a pressure control valve. The thus released nitrogen oxides can be subjected to a regeneration procedure, where they are regenerated to the oxoacid of nitrogen, e.g. nitric acid, by the action of oxygen and water. The thus regenerated oxoacid of nitrogen, e.g. nitric acid, can subsequently be fed back into the process according to the present invention.

The alkylmercaptan, dialkyldisulfide and/or dialkylpolysulfide can be fed into the reactor either as a pure compound, in particular as a single compound, especially as a pure single compound, or as a mixture of pure compounds, i.e. a mixture of an alkylmercaptan, dialkyldisulfide and/or dialkylpolysulfide. In addition, it is also possible, to use a feed stream containing an alkylmercaptan, dialkyldisulfide and/or dialkylpolysulfide, and further compounds. However, said further compounds should be inert under the conditions applied in the oxidation reaction. Thus, any further compounds feed stream in addition to an alkylmercaptan, dialkyldisulfide and/or dialkylpolysulfide preferably only act as diluents, solvents or emulsifiers for the sulfur containing starting compounds. Suitable further compounds are preferably those which can be separated and in particular easily separated by distillation from the desired alkanesulfonic acid and that have a low vapor pressure. This means that such suitable further compounds preferably do not cause or promote the formation of explosive mixtures in a gas phase which could be either in the reaction mixture or above the reaction mixture of the oxidation reaction. Exemplary inert compounds, recited without limitation, are sulfoxide and dimethyl formamide. In order to encompass the feeding of alkylmercaptan, dialkyldisulfide and/or dialkylpolysulfide in any conceivable form, in particular as a pure single compound, as a mixture of pure compounds or as part of a feed stream, into the nitric acid provided in the reactor or into the reactor or into a reaction mixture is hereinafter also referred to as feeding of an alkylmercaptan, dialkyldisulfide and/or dialkylpolysulfide containing stream.

According to the present invention the oxoacid of nitrogen, e.g. nitric acid, is always present in an at least stoichiometric amount relative to the alkylmercaptan, dialkyldisulfide and/or dialkylpolysulfide during the start-up phase of the plant. In order to oxidize said alkylmercaptan, dialkyldisulfide and/or dialkylpolysulfide to the corresponding alkanesulfonic acid as completely as possible, it is therefore preferred to provide the oxoacid of nitrogen, e.g. nitric acid, in the reactor first, and thereafter the alkylmercaptan, dialkyldisulfide and/or dialkylpolysulfide is fed into the oxoacid of nitrogen, e.g. nitric acid, or a liquid phase containing said acid. This procedure allows the adjustment of the amount of the sulfur containing starting compound thus ensures that the oxoacid of nitrogen, e.g. nitric acid, is always present in an at least stoichiometric amount relative to a sulfur containing starting compound fed into the reactor. Whether the oxoacid of nitrogen, e.g. nitric acid, is indeed present in an at least stoichiometric amount relative to the respective sulfur containing starting compound fed into the reactor can be easily determined on the basis of the amount of the oxoacid of nitrogen, e.g. nitric acid, solution provided in the reactor and the concentration of the oxoacid of nitrogen, e.g. nitric acid, in said solution as well as on the amount of the one or more sulfur containing starting compound or the concentration of said compounds in the feed stream fed in. In case the amount of oxoacid of nitrogen, e.g. nitric acid, provided in the reactor is not enough to oxidize the alkylmercaptan, dialkyldisulfide and/or dialkylpolysulfide completely to the corresponding alkanesulfonic acid during the start-up phase of the plant, additional oxoacid of nitrogen, e.g. nitric acid, is fed into the reactor in order to complete said oxidation reaction.

The start-up phase of the process according to the present invention does not require any heat supply. Rather, the release of reaction heat is kept to a minimum during the feeding of an alkylmercaptan, dialkyldisulfide and/or dialkylpolysulfide into the provided oxoacid of nitrogen, e.g. nitric add. Thus, the formation of explosive mixtures in the gas phase is significantly minimized or even avoided. It is therefore a further advantage of providing the oxoacid of nitrogen, e.g. nitric acid, first and then feeding the alkylmercaptan, dialkyldisulfide and/or dialkylpolysulfide, that the feeding rate of a sulfur containing starting compound can be adjusted so that the reaction heat released in the oxidation of said sulfur containing starting compound is kept below a specific maximum reaction temperature. Said temperature maximum is defined by the lowest boiling point of the one or more sulfur containing starting compounds or, when a feed stream with a sulfur containing starting compound is used, by the lowest boiling point of any further inert compound in said feed stream, when it has a lower boiling point than any of the sulfur containing starting compounds. It is therefore preferred to perform the feeding of the alkylmercaptan, dialkyldisulfide and/or dialkylpolysulfide, and particular the feeding of the alkylmercaptan, dialkyldisulfide and/or dialkylpolysulfide into the provided oxoacid of nitrogen, e.g. nitric add, with a feeding rate thus that the reaction heat released in the oxidation of the alkylmercaptan, dialkyldisulfide and/or dialkylpolysulfide is kept below the lowest boiling temperature of any of the compounds fed in. The temperature in the product mixture obtained from the oxidation of the sulfur containing starting compound is monitored by means of a thermometer or any other temperature measurement device known by the skilled person.

In principle, the process according to the present invention is not limited with respect to the type of reactor and with respect to the performance mode of the start-up phase of the plant. Therefore, the start-up phase of the plant in the process according to the present invention can be performed in a batch-mode, a semi-continuous mode and/or a continuous mode. Although a continuous mode is possible, this would increase the start-up time and also result in the loss of off-spec product as well as nitric acid from the reaction system.

In one embodiment of the process according to the present invention, the said start-lip phase of the plant is performed in a hatch mode or in a semi-continuous mode.

In the context of the present invention, the term batch mode is used in accordance to the common knowledge of the person skilled in the art of chemical engineering and denotes the mode of operating a reactor where only a reactant or a mixture of reactants is fed into the reactor during the production but no product or product mixture is removed from the reactor. In a batch mode, said reactant or said mixture of reactants is fed preferably step-wise, for example drop-wise or dosed, into the reactor in order to control the release of reaction heat.

By comparison, in the context of the present invention, the term continuous mode is used in accordance to the common knowledge of the person skilled in the art of chemical engineering and denotes the mode of operating a reactor, where the feeding of a reactant or a mixture of reactants into the reactor and the removal of a product or product mixture are performed simultaneously.

In the context of the present invention, the term semi-continuous is used to denote a mode of operating a reactor, where the feeding of a reactant or a mixture of reactants into the reactor is performed continuously but no product or product mixture is removed from the reactor.

According to the present invention the oxoacid of nitrogen, e.g. nitric acid, is present in an at least stoichiometric amount relative to the alkylmercaptan, dialkyldisulfide and/or dialkylpolysulfide during the start-up phase of the plant. In said start-up phase the oxoacid of nitrogen, e.g. nitric acid, is the sole oxidizing agent for the one or more sulfur containing starting compounds and also for any intermediates resulting from the initial oxidation of any of said compounds. However, the further use of an oxoacid of nitrogen, e.g. nitric acid, in the further operating of the plant would lead to a high water content in said alkanesulfonic acid. This would either limit the scope of application for the thus obtained alkanesulfonic acid or the water has to be removed from the alkanesulfonic acid, in particular through distillation, which however is very energy intensive. It is therefore preferred to perform the further preparation of an alkanesulfonic acid after the start-up phase by oxidation of a corresponding sulfur containing starting compound with oxygen or an oxygen containing fluid, such as ordinary air or air enriched with molecular oxygen, in the presence of catalytic amounts of nitrogen oxides dissolved in the liquid reactor content.

However, while the higher dialkyldisulfides and most of the dialkylpolysulfides have relatively high boiling points, the lower dialkylsulfides already boil at temperatures of around 100° C., and most of the lower alkylmercaptans are either gaseous or highly volatile at the oxidation conditions. For example dimethyldisulfide has a boiling point of 110° C., methylmercaptan is already a gas at a temperature of 6° C., ethylmercaptan boils at 35° C., 2-propylmercaptan boils at 51° C. to 53° C. and 1-propylmercaptan boils at 68° C. (each boiling point or range given for a pressure of 1 bara). Thus, depending on the choice of the sulfur containing starting compound fed in, said sulfur containing starting compound may vaporize and come into direct contact with gaseous oxygen. The ignition point of the thus formed mixture of organic vapors and oxygen is influenced by the oxygen concentration in said mixture and the pressure with which oxygen is introduced into the system during the continuous mode of preparing alkanesulfonic acid: the higher the oxygen pressure, the lower the ignition temperature of the mixture of organic vapors and oxygen.

It is therefore preferred that after the start-up phase the available inner volume of the reactor, in which the preparation of the alkanesulfonic acid is carried out, is filled completely with the product mixture obtained from the oxidation reaction of the process according to the present invention. Accordingly, the step of feeding an alkylmercaptan, dialkyldisulfide and/or dialkylpolysulfide containing stream into the oxoacid of nitrogen, e.g. nitric acid, provided in the reactor is preferably repeated until the available inner volume of the reactor is completely filled with the product mixture obtained from the oxidation. This procedure either avoids the formation of a gas phase, in which a gaseous sulfur containing compound or another organic compound is in direct contact with oxygen, or at least significantly reduces the size of such a gas phase. If a gas phase forms over the liquid phase or the actual reaction mixture, the volume of this gas phase is very small, and thus the consequences of a potential explosion are unobjectionable. It is possible, for example, for individual gas bubbles to ascend to a region over the reaction mixture. Since, however, the volume of these gas bubbles is negligibly small compared with the reaction mixture or the overall reactor volume, any explosion within the gas bubbles cannot cause harm to the environment.

Therefore, the process according to the present invention comprises the steps i) providing an oxoacid of nitrogen in a reactor,
ii) feeding an alkylmercaptan, dialkydisulfide and/or dialkylpolysulfide containing stream into the oxoacid of nitrogen of step i) to give an alkanesulfonic acid containing product mixture, and
iii) repealing step ii) until the available inner volume of the reactor is filled completely with the alkanesulfonic acid containing product mixture obtained in step ii).

In the context of the present invention the term available inner volume of the reactor is used to denote the inner volume of the reactor which is not taken by any installations inside the reactor, such as the stirring unit, and thus available to be taken by the product mixture obtained from the oxidation reaction.

The oxoacid of nitrogen, e.g. nitric add can be either provided in pure or diluted form, such as solution, for example an aqueous solution of the oxoacid of nitrogen.

Preferably, the amount of oxoacid of nitrogen, e.g. nitric acid, provided in step i) of the process according to the present invention is large enough to completely oxidize the amount of alkylmercaptan, dialkydisulfide and/or dialkylpolysulfide fed in step i and/or iii) to the corresponding alkanesulfonic acid.

It is believed that the oxidation of the sulfur containing starting compound to the alkanesulfonic acid proceeds via a disulfone compound which is then hydrolyzed to give the final reaction product. Typically, the required amount of water for the hydrolysis of the disulfone compound in the start-up phase is already provided together with the oxoacid of nitrogen, in particular when an aqueous solution of an oxoacid of nitrogen is used, especially commercially available nitric acid. Nonetheless, additional amounts of water can also be provided during the start-up phase, e.g. step ii) and/or iii), in order to allow the formation of the alkanesulfonic acid.

However, situations may nevertheless occur in which the initially provided oxoacid of nitrogen, e.g. nitric acid, is not enough for an oxidation of the alkylmercaptan, dialkyldisulfide and/or dialkylpolysulfide as completely as possible. This may happen when a dialkyldisulfide or dialkylpolysulfide is used, which still contains a certain amount of the alkylmercaptan used to prepare the dialkyldisulfide or dialkylpolysulfide, and thus, a larger amount of oxoacid of nitrogen, e.g. nitric acid, than expected is required to oxidize the alkylmercaptan to the respective dialkyldisulfide, followed by further oxidation of the thus obtained dialkyldisulfide to the corresponding alkanesulfonic acid. Situations, where the initially provided oxoacid of nitrogen, e.g. nitric acid, is not enough for a complete oxidation of a sulfur containing starting compounds can be monitored through the temperature development: the temperature drops even though further sulfur containing starting compound is added because there is no or not enough oxoacid of nitrogen, e.g. nitric acid, present to successfully continue the oxidation reaction. In that case additional oxoacid of nitrogen, e.g. nitric acid, is fed into the reactor in order to continue the oxidation reaction or to complete said reaction.

Therefore, the process according to the present invention comprises the step iv) feeding additional oxoacid of nitrogen into the reactor, when the amount of oxoacid of nitrogen provided in step i) is not enough to fill the available inner volume of the reactor completely with the product mixture obtained in step ii).

In addition to the rapid oxidation of an alkylmercaptan, dialkyldisulfide and/or dialkylpolysulfide to the corresponding alkanesulfonic acid, the use of an oxoacid of nitrogen in the start-up phase of a plant for the preparation of an alkanesulfonic acid also has the effect of passivating the alloy of the reactor of said plant. After the alloy of the reactor has been passivated the further preparation of alkanesulfonic acid can be continued with an oxidizing agent other than an oxoacid of nitrogen, e.g. nitric acid, for example an oxygen containing fluid is preferably used in the further preparation of an alkanesulfonic acid after the start-up phase. Said oxygen containing fluid can be either a gas stream, such as air, optionally enriched oxygen, or pure oxygen, or it can be a liquid stream, such as a liquid sulfur-containing starting compound which has been mixed with oxygen or air. Alternatively, said gas or liquid stream can also contain a compound which easily releases oxygen into the reaction mixture. Further, the oxygen containing fluid stream is only fed into the reactor, when the available inner volume of said reactor is completely filled with the product mixture obtained in the oxidation of the sulfur containing starting compound. Without wishing to be bound to a specific theory it is believed that the thus fed in oxygen converts the nitrogen monoxide formed in the oxidation of the sulfur containing starting compound with nitric acid to nitrogen dioxide. It is also believed, without wishing to be bound to a specific theory, that the thus formed nitrogen dioxide is regenerated with water to oxoacid of nitrogen, e.g. nitric acid, which is again available for a further rapid oxidation of the sulfur containing starting compound. It is further believed, without wishing to be bound to a specific theory, that the nitrogen dioxide also facilitates the solvation and absorption of oxygen in the product mixture. This facilitates the oxidation of the sulfur containing starting compounds fed into the reactor to give an alkanesulfonic acid containing product mixture.

Therefore, the process according to the present invention comprises the step (v) feeding an oxygen containing fluid stream into the reactor, when the available inner volume of the reactor is completely filled with the product mixture obtained in the step ii) and/or in the step iii).

Oxidation of a sulfur containing starting compound by means of a gas stream enriched with oxygen has the advantage that a gas stream which is more cost-effective, relative to pure oxygen, is fed into the reaction. Further, in line with the course of the oxidation reaction, the amount of oxygen in said gas stream can be adjusted in order to provide for a complete oxidation of the sulfur containing starting compound to the corresponding alkanesulfonic acid. In the simplest case, this gas stream has a higher oxygen content than typical air, in particular room than 20.9 vol.-% of oxygen.

By feeding a gas stream with more than 21 vol.-% of oxygen into the reactor, it is ensured both that there is a very substantially complete oxidation of a sulfur containing starting compound to the corresponding alkanesulfonic acid and that there is a regeneration at the nitrogen oxides ($NO_x$) to the oxoacid of nitrogen, e.g. nitric acid. The thus regenerated oxoacid of nitrogen, e.g. nitric acid, serves then again as the catalyst or the reagent in the oxidation reaction.

It was further found that the passivating effect of the oxoacid of nitrogen, in particular nitric acid, in the process according to the present invention can also be accomplished when the amount of oxoacid of nitrogen, in particular nitric acid, initially provided in the step i) is large enough to provide a final nitrogen dioxide concentration of more than 0.1 wt.-% in the completely filled available inner volume of the reactor (see example 1). Said nitrogen dioxide concentration was found to be sufficient for a later oxidation with an oxygen containing fluid as the sole oxidizing agent continuously fed into the reactor. Notwithstanding the oxoacid of nitrogen, in particular nitric acid, provided in the reactor should be still in at least stoichiometric ratio relative to the sulfur containing starting compound. In this context the aforementioned definitions with respective to the type of sulfur containing starting compound also apply. After the provided oxoacid of nitrogen, in particular nitric acid, has been consumed by said sulfur containing starting compound to give an alkanesulfonic add containing product mixture an oxygen containing fluid stream is fed into the thus obtained product mixture. It is believed that this step either leads to an at least partial regeneration of the oxoacid of nitrogen, in particular nitric acid, which is then again available for the oxidation of any further sulfur containing starting compound, or to the oxidation of the nitrogen monoxide to nitrogen dioxide, which is believed to facilitate the dispersion of the oxidizing agent oxygen in the product mixture.

In any case, the amount of oxoacid of nitrogen, e.g. nitric acid, initially provided in step i) of the process according to the present invention should be large enough to provide for a concentration of more than 0.1 wt.-% of nitrogen dioxide in the completely filled inner volume of the reactor. The amount of nitric acid, which is to be initially provided in step i) of the process and which is required to give a concentration of more than 0.1 wt.-% of nitrogen dioxide in the completely filled inner volume of the reactor, is governed by the inner volume of the reactor and the density of the formed alkanesulfonic acid. In a generalized form the required amount of nitric acid, as one example of an oxoacid of nitrogen, in order to yield a specific concentration of nitrogen dioxide in the filled reactor is given by the following equation:

$$HNO3 \ [mol] = \frac{\text{available inner volume reactor } [l] * \text{density (alkanesulfonic acid)}\left[\frac{kg}{l}\right] * c(NO2)}{\text{molar weight of NO2 }\left[\frac{kg}{mol}\right]}$$

wherein the molar weight of $NO_2$ is 0.046 kg/mol, the density of methanesulfonic acid is 1.48 kg/l, the density of methanesulfonic acid is 1.35 kg/l and c is the desired concentration of the $NO_2$ when the reactor is completely filled with the product mixture obtained from the oxidation of the sulfur containing starting compound, said concentration is more than 0.1 wt.-%, preferably said concentration is from 0.5 to 20 wt.-%.

For example, when the inner volume of the reactor is 100 liters, which is to be filled completely with the reaction product methanesulfonic acid, a nitrogen dioxide concentration of 2 wt.-% equals 2.96 kg $NO_2$. Accordingly, approximately 4.06 kg or 64.34 mol of nitric acid must be initially provided in step i) of the process according to the present invention. This amount of nitric acid is suitable to oxidize approximately 19.3 mol or ca. 1.82 kg of dimethyldisulfide to methanesulfonic acid.

Therefore, at least the amount of nitric acid according to the formula nitric acid [mol]>(available inner reactor volume [I]*density of the alkanesulfonic acid [kg/l]*0.01)/molar weight of nitrogen dioxide [kg/mol] is provided in the reactor for the star-up phase of the process according the present invention.

The presence of even small amounts of nitrogen dioxide in the reaction product has the effect that the self-ignition temperature of the sulfur containing starting compound in oxygen, in particular of the dimethyldisulfide in oxygen, is significantly reduced.

After provision of the oxoacid of nitrogen, e.g. nitric acid, the respective sulfur containing starting compound is dosed into the oxoacid of nitrogen, e.g. nitric acid, so that the acid is consumed in the oxidation of the sulfur containing starting compound. This oxidation reaction leads to a release of reaction heat. Therefore, the start and the end of the oxidation of the sulfur containing starting compound by the oxoacid of nitrogen, e.g. nitric acid, can be followed by means of the increase or the decrease of the temperature in the reactor. Hence, the total consumption of the oxoacid of nitrogen, e.g. nitric acid, initially provided in the reactor is indicated by a decrease of the temperature in the reactor. After the consumption of the initially provided oxoacid of nitrogen, e.g. nitric acid, the dosing of an oxygen containing fluid stream into the obtained product mixture is started in order to continue and maintain the oxidation reaction.

In one embodiment of the process according to the present invention the oxoacid of nitrogen is nitric acid and the process comprises the further steps i') providing at least the amount of nitric acid according to the formula nitric acid [mol]>(available inner reactor volume [I]*density of the alkanesulfonic acid [kg/l]*0.01)/molar weight of nitrogen dioxide [kg/mol] in a reactor, ii') feeding an alkylmercaptan, dialkyldisulfide and/or dialkylpolysulfide containing stream into the nitric acid of step i') to give an alkanesulfonic acid containing product mixture, and iv') after consumption of the nitric acid in step ii) feeding an oxygen containing fluid stream into the alkanesulfonic acid containing product mixture to give an alkanesulfonic acid containing product mixture.

In this embodiment the nitric acid provided in step i') is consumed by the sulfur containing starting compound fed in step ii'), and thus the nitric acid is converted to nitrogen monoxide. Without wishing to be bound to a specific theory it is believed that the feeding of an oxygen containing fluid stream into the product mixture of step ii') leads to an oxidation of the nitrogen monoxide to give nitrogen dioxide. It is further believed that that the thus formed nitrogen dioxide either facilitates the solvation of the fed in oxygen in the liquid phase of the product mixture or acts as a catalyst in the oxidation of the sulfur containing starting by the oxygen.

A good introduction and in particular dispersion of the oxygen containing fluid stream into the liquid phase in the reactor is necessary to perform the further oxidation of the sulfur containing starting compound with said oxygen containing fluid. It is therefore advantageous that either the stirrer of the reactor is immersed into the liquid phase as completely as possible or that the oxygen containing fluid stream is fed into the reactor at a point adjacent to the lower end of the reactor. In the latter case the oxygen containing fluid is preferably fed into the reactor via a frit at the bottom of the reactor, although a tube or ring or combinations of these gas spargers can also be used to provide a good dispersion of the oxygen in the liquid phase. Furthermore, in order to optimize the dispersion of the oxygen in the liquid phase, the gas sparging device is located within an impellers diameter next to, or above, or preferably directly below the stirrer.

When the liquid phase comprising the nitric acid initially provided in step i') and the sulfur containing starting compound fed in step ii') is not enough to completely immerse the stirrer of the reactor, water and/or further nitric acid is fed into the reactor, until the stirrer of the reactor is immersed in the liquid phase.

In a preferred embodiment the process according to the present invention further comprises the step iii') feeding water and/or further nitric acid into the reactor until the stirrer of the reactor is immersed in the alkanesulfonic acid containing product mixture.

Preferably, the water and/or further nitric acid is fed into the reactor in step ii') until a quarter, a third, or half of the available inner volume of the reactor is filled with the resulting liquid phase. Thus it is ensured that the stirrer of the reactor is always immersed in the liquid phase so that an introduction, mixing and dispersion of the oxygen containing fluid into the liquid phase is possible.

Provided that a good introduction and in particular dispersion of the oxygen containing fluid stream into the liquid phase in the reactor is given, the embodiment of the process according to the present invention further comprises the step of v') feeding an alkylmercaptan, dialkyldisulfide and/or dialkylpolysulfide containing stream and an oxygen containing fluid stream into the reactor until the available inner volume of the reactor is filled completely with the alkanesulfonic acid containing product mixture.

It has proved to be particularly advantageous that after the start-up phase the further oxidation of a sulfur containing starting compound with oxygen is performed in a solution of the alkanesulfonic acid to be prepared. Alkanesulfonic acids have high boiling points, for example methanesulfonic acid has a boiling point of about 167° C. at 13 hPa. Thus, the alkanesulfonic acid already prepared in the preceding oxidation reaction of steps ii) and iii) or steps ii') to iv') of the process according to the present invention serves as a high boiling solvent which absorbs the oxidation heat released in the oxidation of the sulfur containing starting compound. Thus, the appearance of hot spots, i.e. areas of local overheating, in the reactor is avoided or at least significantly reduced. As a consequence, the risk of ignition of highly flammable compounds in the reaction mixture is either avoided or at least significantly reduced. This allows the inexpensive production of an alkanesulfonic acid in high-yields under safety-relevant aspects.

For performing the oxidation of an alkylmercaptan, dialkyldisulfide and/or dialkylpolysulfide in a solution of the alkanesulfonic acid to be prepared, a part of the alkanesulfonic acid containing product mixture obtained in steps ii) and iii) or in steps ii') to iv') of the process according to the present invention is removed from the reactor, and further alkylmercaptan, dialkyldisulfide and/or dialkylpolysulfide is fed into the reactor to yield a reaction mixture, which is subsequently reacted to an alkanesulfonic acid containing product mixture. In order to provide for a uniform product, said alkylmercaptan, dialkyldisulfide and/or dialkylpolysulfide is preferably identical with the alkylmercaptan dialkyldisulfide and/or dialkylpolysulfide which has been subjected to the preceding oxidation reaction in the reactor.

Therefore, the process according to the present invention comprises the steps vi) removing at least part of the alkanesulfonic acid containing product mixture from the reactor, and vii) feeding an alkylmercaptan, dialkyldisulfide and/or dialkylpolysulfide containing stream into the reactor to yield a reaction mixture, wherein said alkylmercaptan, dialkyldisulfide and/or dialkylpolysulfide is identical with the alkylmercaptan, dialkyldisulfide and/or dialkylpolysulfide of any of the preceding step.

The feeding of an oxygen containing fluid into the alkanesulfonic acid containing product mixture is (of course) continued in order to maintain the oxidation reaction of the sulfur containing starting compound to an alkanesulfonic acid or alkanesulfonic acid containing product mixture.

Preferably, the concentration of the alkylmercaptan, dialkyldisulfide and/or dialkylpolysulfide in the reaction mixture is not more than 20 weight-% and the concentration of the additional or optional alkanesulfonic acid which serves as a solvent is more than 70 weight-% in said reaction mixture. This has the advantage that the oxidation of the sulfur containing starting compounds to the desired alkanesulfonic acid proceeds rather smoothly. The use of an alkanesulfonic acid as solvent which is also the target compound of the process has the further advantage that there is no need to separate the solvent from the product. Consequently, the purification by distillation of the crude product, i.e. the product mixture which is removed from the reactor, is significantly less complex and energy intensive. In the context of the present invention the term not more than 20 weight-% is used to denote all conceivable values from more than 0 weight-% up to and including 20 weight-%. Therefore, said term encompasses not only the integral values 1, 2, 3, 4, 5, 6, 7, 8, 9, 10, 11, 12, 13, 14, 15, 16, 17, 18, 19 and 20 weight-% but also all values from greater than 0 weight-% up to and including 20 weight-% that can be expressed by real numbers.

Preferably, the continuous oxidation of an alkylmercaptan, dialkyldisulfide and/or dialkylpolysulfide with an oxygen containing fluid stream is performed in the presence of a catalytic amount of nitric acid. In particular, the ratio of the alkylmercaptan, dialkyldisulfide and/or dialkylpolysulfide to nitric acid ranges from 2000:1 (mol/mol) to less than 1:2 (mol/mol). Said ratio encompasses all ratios which can be expressed by integral and real numbers, from inclusive of 2000:1 (mol/mol) to less than 1:2 (mol/mol), and said ratio expressively encompasses but is not limited to the ratios 2000:1 (mol/mol), 1000:1 (mol/mol), 500:1 (mol/mol), 200:1 (mol/mol), 100:1 (mol/mol), 90:1 (mol/mol), 80:1 (mol/mol), 70:1 (mol/mol), 60:1 (mol/mol), 50:1 (mol/mol), 40:1 (mol/mol), 30:1 (mol/mol), 20:1 (mol/mol), 10:1 (mol/mol), 5:1 (mol/mol), and 2:1 (mol/mol).

It is a further advantage of the use of an alkanesulfonic acid as solvent in combination with the use of a catalytic amount of oxoacid of nitrogen, e.g. nitric acid, that only the quantity of water, which is indeed necessary for the hydrolysis of the dialkyldisulfone to the alkanesulfonic acid, needs to be introduced into the reaction. This allows the preparation of a substantially anhydrous alkanesulfonic acid. The final purification by distillation of the crude alkanesulfonic acid obtained from the process according to the present invention therefore primarily only serves for the purpose of cleaning the desired alkanesulfonic acid from impurities in the trace range and from nitrogen oxides resulting from the consumption of the oxoacid of nitrogen, e.g. nitric acid, in the oxidation reaction or its thermal decomposition. Thus, the distillation of the crude alkanesulfonic acid requires not only less complexity of apparatus, but also less energy, and the capital and energy costs of the process according to the present invention are therefore significantly lower than in the case of the processes of the prior art (e.g. WO 00/31027), where the continuous preparation of alkanesulfonic acid is done with a stoichiometric excess of nitric acid.

When at least a part of the alkanesulfonic acid containing product mixture is removed from the reactor and replaced with a new alkylmercaptan, dialkyldisulfide and/or dialkylpolysulfide or a volume stream containing new alkylmercaptan, dialkyldisulfide and/or dialkylpolysulfide, the formation of a continuous gas phase of a sulfur containing starting compound and oxygen should be avoided.

Therefore, in the process according to the present invention the volume of the alkylmercaptan, dialkyldisulfide and/or the dialkylpolysulfide containing stream, fed into the reactor in step vii), equals the volume of the product mixture removed from the reactor in step vi).

Preferably, the alkylmercaptan, dialkyldisulfide and/or the dialkylpolysulfide containing stream of step vii) additionally contains an alkanesulfonic acid, which is identical with the alkanesulfonic acid to be prepared in order to provide for a reaction mixture with a concentration of the alkylmercaptan, dialkyldisulfide and/or dialkylpolysulfide of not more than 20 weight-% and a concentration of the additional or optional alkanesulfonic acid of more than 70 weight-% in said reaction mixture.

In case the oxidation of the sulfur containing starting compounds in steps ii) and iii) of the process according to the present invention did proceed completely or virtually completely, it is alternatively also possible to remove at least a part of the alkanesulfonic acid containing product mixture from the reactor and first feed a sulfur containing starting compound into the reactor and subsequently feed an oxygen containing fluid stream into the reactor.

In an alternative embodiment of the process according to the present invention the sequence of the step v) and the steps vi) to vii) is therefore changed.

When an alkanesulfonic acid shah be produced on a large industrial scale, it is advantageous to perform the further production of an alkanesulfonic acid, i.e. the production of an alkanesulfonic acid after the startup phase, in a continuous mode or in an essentially continuous mode.

In another preferred embodiment of the process according to the present invention the steps v) to vii) or v') to vii) are therefore performed in a continuous mode or in, en essentially continuous mode.

In the context of the present invention the term essentially continuous mode is used to denote the mode of operating a reactor, where the feeding of a reactant or a mixture of the reactants into the reactor and the removal of a product or a product mixture are performed mainly at the same time, however accompanied by short episode of a batch or semi-continuous mode of operation of the reactor.

After the available inner volume of the reactor is completely filled with the alkanesulfonic acid containing product mixture, further preparation of an alkanesulfonic acid is preferably carried out at a reaction temperature of not more than 90° C. This has the effect that the precipitation of elemental sulfur is avoided. Said precipitation of elemental sulfur is believed to result from a side-reaction, e.g. a synproportionation, sometimes also called compromportionation, of fully oxidized reaction intermediates, such as R—S—$SO_2$—R, or from a side-reaction of a not hydrolyzed dialkyldisulfone R—$SO_2$—$SO_2$—R. A further advantage of a reaction mixture of not more than 90° C. is that no explosion-prone gas mixtures with oxygen are formed. The further, in particular continuous, preparation of an alkanesulfonic acid is preferably performed at a reaction temperature of 30° C.+/−5° C. to 90° C.

The further, and in particular continuous, preparation of an alkanesulfonic acid is not subject to any restrictions regarding the pressure, in particular the pressure with which an oxygen containing fluid stream is introduced into the reactor. In principle, the upper pressure limit is determined by the pressure resistance of the reactor. Since high or very high pressures require complicated and costly reactors, the further, and in particular continuous, preparation of an alkanesulfonic acid is preferably done at pressures of not more than 100 bare. In the context of the present invention the term bare is synonymous with bar absolute and is used as the unit for the absolute pressure. In accordance with the common knowledge of the skilled person, the absolute pressure is measured without taking account of the prevailing air pressure, in other words absolutely relative to the zero pressure in empty space. Preferably, the further, and in particular continuous, preparation of an alkanesulfonic acid is done at a superatmospheric pressure. In the context of the present invention, the term superatmospheric pressure is used to denote all pressures of more than 1 bare that can be expressed using integral or real numbers. In practice, however, a pressure of 20 bare leads neither to an increase in the yield nor to a faster completion of the oxidation reaction. Therefore, the further or continuous preparation of an alkanesulfonic acid is performed at a pressure of more than 1 bara and up to 20 bara.

In order to provide for a good mixing of the sulfur containing starting compound with the oxidizing agent irrespective of whether said oxidizing agent is the initially provided oxoacid of nitrogen, e.g. nitric acid, or the oxygen which is later fed into the reactor, the oxoacid of nitrogen, e.g. nitric acid, and/or the oxygen containing fluid stream or any further compound, preferably the additional alkanesulfonic acid used as diluent or solvent, one or more of said compounds is preferably fed into the reactor at a point adjacent to the lower end of the reactor. A feeding of any of said compounds into the reactor at a point adjacent to the lower end of the reactor can be accomplished through an immersion tube, which is optionally equipped with a frit at its opening end in order to provide for a good distribution of the reactant into the solution. In particular, the oxygen containing fluid stream is fed into the reactor at a point adjacent to the lower end of the reactor. This has the advantage that the gaseous oxygen ascends through the solution and is thus homogeneously distributed throughout the whole solution. It is particularly preferred that the oxygen containing fluid stream is fed into the reactor near to or under the stirrer of the reactor. This leads to a very good introduction, mixing and dispersion of the oxidizing agent within the reaction solution. Preferably, the oxygen containing fluid stream is therefore fed in by means of a frit or any other suitable gas sparging device known to those skilled in the art.

In yet a further, preferred embodiment of the process according to the present invention the oxygen containing fluid stream is fed into the reactor near to or under the stirrer of the reactor.

It is also of particular relevance to provide for an excess or at least stoichiometric amount of oxoacid of nitrogen, e.g. nitric acid, relative to the alkylmercaptan, dialkyldisulfide and/or dialkylpolysulfide during the shut-off phase of the plant. Further, it is also important to avoid the formation of a continuous gas phase of a sulfur containing starting compound in direct contact with oxygen in order to avoid any explosion-prone situations during the shut-off phase of the plant. In order to initiate a safe shut-off phase of the plant, the feeding of the oxygen containing fluid stream into the reaction mixture is therefore terminated first prior to all other steps of the shut-off phase. Preferably, this effect is achieved by stopping the feeding of the alkylmercaptan, dialkyldisulfide and/or dialkylpolysulfide containing stream into the reactor. As a further benefit of this procedure the formation of a complex mixture is avoided, which otherwise had to be subjected to a complex purification procedure. In order to provide for a complete oxidation of the remaining amount of sulfur containing starting compound in the reactor, additional oxoacid of nitrogen, e.g. nitric acid, is fed into the reactor.

Alternatively, a safe-shut-off phase of the plan is initiated by stopping the feeding of a sulfur containing starting compound into reactor. The stirrer is still working and the feeding of an oxygen containing fluid stream into the reactor is continued. Optionally, the flow exiting the reactor is stopped in order to operate the reactor is batch mode. When there is no more oxygen consumption within the reactor due the complete conversion of the sulfur containing starting compound to the corresponding alkanesulfonic acid, the feeding of an oxygen containing fluid stream into the reactor is stopped. The point at which there is no more oxygen consumption in the reactor is evident from the cessation of the exothermic reaction and as a consequence the reactor cools down.

In general, the completion or at least virtual completion of the oxidation reaction of the sulfur containing starting compound to the desired alkanesulfonic acid can be monitored by means of the temperature development with a thermometer: when all of the sulfur containing starting compound has been reacted to the alkanesulfonic acid, there is no further release of reaction heat upon addition of further oxoacid of nitrogen, e.g. nitric acid; rather, the temperature of the product mixture in the reactor drops or remains constant. In that case, the alkanesulfonic acid containing product mixture can be finally removed from the reactor.

It is therefore preferred that an alkanesulfonic acid containing product mixture is removed from the reactor after an at least virtually complete oxidation of the alkylmercaptan, dialkyldisulfide and/or dialkylpolysulfide to the corresponding alkanesulfonic acid. In order to achieve said complete or at least virtually complete oxidation of the sulfur containing compound, the reactor is preferably operated in batch mode during the shut-off phase of the plant.

In principle, the present invention is not subject to any restrictions on the size of the alkylradical of the alkylmercaptan, dialkyldisulfide and/or dialkylpolysulfide provided that the respective sulfur containing starting compound is a liquid at room temperature or at the reaction temperature or soluble in the nitric acid provided in the reactor or in the alkanesulfonic acid to be prepared. Each of the alkyl radicals is either linear or branched, preferably linear, and is preferably a $C_1$ to $C_{12}$ alkyl radical, especially a $C_1$ to $C_6$ alkyl radical or a $C_1$ to $C_4$ alkyl radical, optionally substituted by radicals which are not reactive under conditions for oxidation reactions. The alkyl radical of the sulfur containing starting compound is preferably selected from the group consisting of methyl, ethyl, n-propyl, iso-propyl, n-butyl, iso-butyl and tert-butyl. In case an alkanesulfonic acid is prepared from two or more of the group alkylmercaptan, dialkyldisulfide and dialkylpolysulfide, the alkyl radicals of each of the sulfur containing starting compounds are identical in order to provide for a uniform reaction product, i.e. only a single main product, in case an alkanesulfonic acid is prepared from a dialkyldisulfide and/or dialkyldisulfide the alkyl radical of these compounds are always identical, in other words an alkanesulfonic acid is prepared from a symmetrical dialkydisulfide and/or a symmetrical dialkylpolysulfide.

Thus, in an embodiment of the process according to the present invention the alkanesulfonic acid is prepared from an alkylmercaptan, dialkyldisulfide and/or dialkylpolysulfide with a $C_1$ to $C_{12}$ alkyl radical.

Preferably, in the process according to the present invention an alkanesulfonic acid is prepared by oxidation of a dialkyldisulfide, wherein each of the alkyl radicals has from one to twelve alkyl radicals. The economically most relevant alkanesulfonic acid is methanesulfonic acid.

Therefore, in a preferred embodiment of the process according to the present invention methanesulfonic acid is prepared by oxidation of methylmercaptan, dimethyldisulfide and/or dimethylpolysulfide.

Particularly preferred is the preparation of methanesulfonic acid by oxidation of dimethyldisulfide.

The process according to the present invention has successfully proven that the use of an oxoacid of nitrogen, e.g. nitric acid, containing liquid phase in the preparation of an alkanesulfonic acid by oxidation of an alkylmercaptan, a dialkyldisulfide and/or a dialkylpolysulfide does not only facilitate the rapid oxidation of the starting compounds, which also leads to an inhibition of otherwise occurring corrosion phenomena. Rather, the use of an oxoacid of nitrogen, e.g. nitric acid, containing liquid phase also leads to a passivation of the alloy of the respective reactor for the oxidation an alkylmercaptan, dialkyldisulfide and/or dialkylpolysulfide.

The present invention is further described by the following items:

1. Process for operating a plant for preparing an alkanesulfonic acid, wherein said alkanesulfonic acid is prepared by oxidation of an alkylmercaptan, dialkydisulfide and/or dialkylpolysulfide, characterized in that the oxidation is performed in the presence of an at least stoichiometric amount of an oxoacid of nitrogen relative to the amount of said alkylmercaptan, dialkyldisulfide and/or dialkylpolysulfide during the start-up phase of the plant.
2. Process according to item 1, wherein the start-up phase of the plant is performed in a batch mode or in a semi-continuous mode.
3. Process according to item 1 or 2, wherein the start-up phase of the plant comprises the steps
   i) providing an oxoacid of nitrogen in a reactor,
   ii) feeding an alkylmercaptan, dialkydisulfide and/or dialkylpolysulfide containing stream into the oxoacid of nitrogen of step i) to give an alkanesulfonic acid containing product mixture, and
   iii) repeating step ii) until the available inner volume of the reactor is filled completely with the alkanesulfonic acid containing product mixture obtained in step ii).
4. Process according to item 3, further comprising the step
   iv) feeding additional oxoacid of nitrogen into the reactor, when the amount of oxoacid of nitrogen provided in step i) is not enough to fill the available inner volume of the reactor with the product mixture obtained in step ii).
5. Process according to item 3 or 4, further comprising the step
   v) feeding an oxygen containing fluid stream into the reactor, when the available inner volume of the reactor is completely filled with the product mixture obtained in the step ii) and/or in the step iii).
6. Process according to item 1 or 2, wherein the oxoacid of nitrogen is nitric acid and the process further comprises the steps
   i') providing at least the amount of nitric acid according to the formula $$\text{nitric acid [mol]} > \frac{(\text{available inner volume reactor [l]} * \text{density alkanesulfonic acid} \left[\frac{\text{kg}}{\text{l}}\right] * 0.01)}{\text{molar weight of nitrogen dioxide} \left[\frac{\text{kg}}{\text{mol}}\right]}$$

in a reactor,
   ii') feeding an alkylmercaptan, dialkyldisulfide and/or dialkylpolysulfide containing stream into the nitric acid of step i') to give an alkanesulfonic acid containing product mixture, and iv') after consumption of the nitric acid in step ii') feeding an oxygen containing fluid stream into the alkanesulfonic acid containing product mixture.

7. Process according to item 6, further comprising the step
   iii') feeding water and/or further nitric acid into the reactor until the stirrer of the reactor is immersed in the alkanesulfonic acid containing product mixture.

8. Process according to item 6 or 7, further comprising the step
   v') feeding an alkylmercaptan, dialkyldisulfide and/or dialkylpolysulfide containing stream and an oxygen containing fluid stream into the reactor until the available inner volume of the reactor is filled completely with the alkanesulfonic acid containing product mixture.

9. Process according to any of items 3 to 8, further comprising the steps
   vi) removing at least part of the alkanesulfonic acid containing product mixture from the reactor, and
   vii) feeding an alkylmercaptan, dialkyldisulfide and/or dialkylpolysulfide containing stream into the reactor to yield a reaction mixture, wherein said alkylmercaptan, dialkyldisulfide and/or dialkylpolysulfide is identical with the alkylmercaptan, dialkyldisulfide and/or dialkylpolysulfide of any of the preceding steps.

10. Process according to item 9, wherein the volume of the alkylmercaptan, dialkyldisulfide and/or dialkylpolysulfide containing stream, fed into the reactor in step vii), equals the volume of the product mixture removed from the reactor in step vi).

11. Process according to any of items 5 to 10, wherein the steps v) to vii) or v') to vii) are performed in a continuous mode or in an essentially continuous mode.

12. Process according to any of items 5 to 11, wherein the oxygen containing fluid stream is fed into the reactor near to or under the stirrer of the reactor.

13. Process according to any of items 1 to 12, wherein alkanesulfonic acid is prepared from an alkylmercaptan, dialkyldisulfide and/or dialkylpolysulfide with a $C_1$ to $C_{12}$ alkyl radical.

The present invention is further illustrated by the following examples.

EXAMPLES

Comparative Example 1

A first test was performed to see the corrosive behavior of a typical reaction mixture of the preparation of an alkanesulfonic acid by oxidizing a dialkyldisulfide with oxygen on the materials of chemical reactors. For this purpose coupons of four different austenitic steels were placed in a bath of a mixture comprising 96.5 wt.-% methanesulfonic acid (MSA), 2 wt.-% dimethyldisulfide (DMDS), 1 wt.-% S-methyl methanethiosulfonate (MMTS) and 0.5 wt.-% water ($H_2O$), which is representative for a reaction mixture obtained in the oxidizing of a dialkyldisulfide with oxygen.

Plates of the following austenitic stainless steels were used in the test:

TABLE 1

Overview of the tested austenitic stainless steels.

| Material number according to EN 10 088-2 | DIN/EN number | ASTM (USA) number |
|---|---|---|
| 1.4404 | X6 CrNiMoTi17-12-2 | 316 L |
| 1.4439 | X 2 CrNiMoN 17-13-5 | S 31726 |
| 1.4539 | X 1 NiCrMoCu 25-20-5 | N08904 |
| 1.4571 | X 6 CrNiMoTi 17-12-2 | 316 Ti |

The thickness of the different coupons was measured before and after the tests. For determining the corrosive effect of dimethyldisulfide and S-methyl methanethiosulfonate on the austenitic stainless steels, the coupons were placed into a mixture comprising 96.5 wt.-% methanesulfonic acid (MSA), 2 wt-% dimethyldisulfide (DMDS), 1 wt.-% S-methyl methanethiosulfonate (MMTS) and 0.5 wt.-% water ($H_2O$) at a constant temperature of 70° C. for a period of 300 hours. The difference in the thickness of the coupons was determined and was converted to a loss of thickness in mm per year (mm/year). The results are summarized, in the table below. None of the chosen austenitic stainless steels was resistant to the mixture of the preparation of methanesulfonic acid. However, there were even strong corrosion effects visible on the steels according to the material numbers 1.4571 and 1.4404.

TABLE 2

Results for the tested austenitic stainless steels

| | Steels tested | | | |
|---|---|---|---|---|
| | 1.4571 | 1.4404 | 1.4539 | 1.4439 |
| Thickness loss | ≥10 mm/year | ≥10 mm/year | up to 10 mm/year | up to 10 mm/year |

Comparative Example 2

A second test was performed in order to find out whether the presence of dimethyldisulfide (DMDS), S-methyl methanethiosulfonate (MMTS) or any other components, such as acetic acid, in the reaction mixture leads to the observed, corrosion phenomena. For this purpose four different solutions based on methanesulfonic acid were provided: a first solution which consisted of pure methanesulfonic acid (MSA 100%), a second solution with methanesulfonic acid containing traces of acetic acid (MSA+AA), a third solution with methanesulfonic acid containing 1 wt.-% of S-methyl methanethiosulfonate (MSA+MMTS) and a fourth solution with methanesulfonic acid containing 2 wt.-% of dimethyldisulfide (MSA+DMDS).

The thickness of the different test coupons of the four different material numbers of comparative example 1 was measured before and after the tests. For determining the corrosive effect of dimethyldisulfide, S-methyl methanethiosulfonate or acetic acid on the austenitic stainless steels, the coupons were placed into the aforementioned solutions at a constant temperature of 70° C. for a period of 300 hours. The difference in the thickness of the four test coupons was determined and then converted to a loss of thickness in mm per year (mm/year). The results are summarized in table 3 below.

TABLE 3

Results for the tested austenitic stainless steels

| | Steels tested | | | |
|---|---|---|---|---|
| | 1.4571 | 1.4404 | 1.4408 | 1.4462 |
| MSA (100%) | <0.01 mm/year | | | |
| MSA + AA | <10 mm/year | | | |
| MSA + AA + MMTS | ≥10 mm/year | | | |
| MSA + AA + DMDS | ≥10 mm/year | | | |

The results show that pure methanesulfonic acid does not lead to considerable corrosion phenomena. However, the additional presence of acetic acid, even if only in traces, already leads to significantly increased corrosion phenomena. The additional presence of the S-methyl methanethiosulfonate or dimethyldisulfide in methanesulfonic acid even leads to thickness loss of the tested steels of approximately 50 mm per year. Hence, the additional presence of any of these sulfur species leads to an increase in corrosion by a factor of more than 1000, compared to the corrosion in pure methanesulfonic acid.

Example 1

In order to find out the necessary amount of nitric acid for passivating steels, test coupons of the material numbers 1.4408, 1.4462, 1.4539 and 1.4571 were placed into different solutions based on methanesulfonic acid with traces of acetic acid: a first solution containing methanesulfonic acid with traces of acetic acid (MSA+AA), a second solution containing methanesulfonic acid with traces of acetic acid and in addition 0.05 wt.-% of nitric acid (MSA+AA+0.05% HNO₃), a third solution containing methanesulfonic acid with traces of acetic acid and in addition 0.1 wt.-% of nitric acid (MSA+AA+0.1% HNO₃), and a fourth solution containing methanesulfonic acid with traces of acetic acid and in addition 0.5 wt.-% of nitric acid (MSA+AA+0.5% HNO₃). The temperature of the solutions was in each case 70° C. and the test coupons were left in the solutions for a duration of 300 hours. The difference in the thickness of the four test coupons before and after the tests was determined according to the procedure of comparative examples 1 and 2 and was converted to a loss of thickness in mm per year (mm/year). The results are summarized in table 4 below.

TABLE 4

Corrosion rates of steels contested with nitric acid containing methanesulfonic acid.

| | Steels tested | | | |
|---|---|---|---|---|
| | 1.4408 | 1.4462 | 1.4539 | 1.4571 |
| MSA + AA | <10 mm/year | | | |
| MSA + AA + 0.05% HNO₃ | pitting corrosion | | | |
| MSA + AA + 0.1% HNO₃ | <0.01 mm/year | <0.01 mm/year | <0.01 mm/year | crevice corrosion |
| MSA + AA + 0.5% HNO₃ | <0.01 mm/year | | | |

The results show that the presence of 0.5 wt.-% of nitric acid passivates the surfaces of all tested steels' against corrosion by methanesulfonic acid with traces of acetic acid.

Example 2

Further tests were carried out to tired out whether the Presence of 0.5 wt.-% of nitric acid is also effective to passivate steels against corrosion by methanesulfonic acid, which in addition to acetic acid also contains 1 wt.-% of S-methyl methanethiosulfonate and 2 wt.-% of dimethyldisulfide. Test coupons of the material numbers 1.4408, 1.4462, 1.4539 and 1.45711 were placed into the solutions, which had a temperature of 70° C., and left therein for a duration of 300 hours. The difference in the thickness of the four test coupons before and after the tests was determined according to the procedure of comparative examples 1 and 2 and then converted to a loss of thickness in mm per year (mm/year). The results are summarized in table 5 below.

TABLE 5

Corrosion rates of steels contacted with methanesulfonic acid containing sulfur compounds and nitric acid.

| | Steels tested | | | |
|---|---|---|---|---|
| | 1.4408 | 1.4462 | 1.4539 | 1.4571 |
| MSA + AA + MMTS | ≥10 mm/year | | | |
| MSA + AA + DMDS | ≥10 mm/year | | | |
| MSA + AA + MMTS + 0.5% HNO₃ | <0.01 mm/year | | | |
| MSA + AA + DMDS + 0.5% HNO₃ | <0.01 mm/year | | | |

It was found that the presence of 0.5% of nitric acid is also effective to passivate the surface of test coupons of the tested steels against corrosion by methanesulfonic acid containing traces of acetic acid and S-methyl methanethiosulfonate or dimethyldisulfide.

Example 3

In situ tests were carried out in order to show the passivating effect of nitric acid on the material of a chemical reactor in the industrial preparation of methanesulfonic acid by oxidation of dimethyldisulfide. For this purpose, a continuously stirred tank reactor (CSTR) was used that effected a conversion of dimethyldisulfide of at least 98%, so that the product stream exiting the reactor contained ca. 1 wt.-% of dimethyldisulfide and ca. 0.5 wt.-% S-methyl methanethiosulfonate. The product stream exiting the reactor was directed to a material test unit, which essentially is a jacketed pressure vessel with a residence time of approximately one hour. Using the jacket it was possible to regulate the temperature within the material test unit from 40° C. to 70° C. This means that the reactor for producing methanesulfonic acid could be operated first at a relatively safe temperature of 40° C. and independently the temperature in the material test unit could be increased to 70° C. Two test coupons of each of the steels according to the material numbers 1.4408 and 1.4507 were attached inside the jacketed pressure vessel using screws made of polytetrafluoroethylene.

The tests were carried out for a complete duration of more than two months. Each test ran for a duration of approximately three days: The operation mode in the reactor and the temperature in the material test unit are summarized in table 6. After each test run the material test unit was opened and the steel test coupons were inspected for signs of corrosion and their weight was noted to quantify any weight losses.

TABLE 6

In situ material testing conditions

| Run no. | Test duration [h] | Cumulated test duration [h] | Operation mode in the reactor | Temperature in the material test unit [° C.] |
|---|---|---|---|---|
| 1 | 145.0 | | 500 g/h DMDS, 40° C., 150 g/h HNO$_3$ (32 wt.-%) | 40 |
| 2 | 68.6 | 214 | 500 g/h DMDS, 40° C., 150 g/h HNO$_3$ (32 wt.-%) | 40 |
| 3 | 65.5 | 279 | 500 g/h DMDS, 40° C., 150 g/h HNO$_3$ (32 wt.-%) | 40 |
| 4 | 71.0 | 350 | 500 g/h DMDS, 40° C., 150 g/h HNO$_3$ (32 wt.-%) | 50 |
| 5 | 69.5 | 420 | 500 g/h DMDS, 40° C., 150 g/h HNO$_3$ (32 wt.-%) | 55 |
| 6 | 72 | 492 | 500 g/h DMDS, 40° C., 150 g/h HNO$_3$ (32 wt.-%) | 60 |
| 7 | 68 | 559 | 500 g/h DMDS, 40° C., 150 g/h HNO$_3$ (32 wt.-%) | 70 |
| 8 | 92 | 651 | 500 g/h DMDS, 50° C., 150 g/h HNO$_3$ (32 wt.-%) | 70 |
| 9 | 69 | 719 | 500 g/h DMDS, 50° C., 150 g/h HNO$_3$ (16 wt.-%) | 70 |
| 10 | 91 | 810 | 500 g/h DMDS, 55° C., 150 g/h HNO$_3$ (32 wt.-%) | 70 |
| 11 | 164 | 974 | 500 g/h DMDS, 60° C., 150 g/h HNO$_3$ (32 wt.-%) | 70 |
| 12 | 90 | 1064 | 760 g/h DMDS, 60° C., 225 g/h HNO$_3$ (32 wt.-%) | 70 |
| 13 | 56 | 1120 | 760 g/h DMDS, 50° C., 195 g/h HNO$_3$(16 wt.-%) | 70 |
| 14 | 42 | 1162 | 760 g/h DMDS, 60° C., 170 g/h HNO$_3$ (8 wt.-%) | 70 |

In all test runs there were no signs of corrosion whatsoever on any of the test coupons and there were no weight losses recorded, even when lower concentrations of nitric acid were dosed, e.g. the amount of nitric acid dosed in test run no. 14 equals a nitric acid concentration of approximately 1 wt.-% in the product stream.

The invention claimed is:

1. A process for operating a plant for preparing an alkanesulfonic acid, wherein said alkanesulfonic acid is prepared by oxidizing an alkylmercaptan, dialkydisulfide and/or dialkylpolysulfide, such that the oxidizing occurs in the presence of an at least stoichiometric amount of an oxoacid of nitrogen relative to an amount of said alkylmercaptan, dialkyldisulfide and/or dialkylpolysulfide during a start-up phase of the plant, the process comprising:
   i) providing an oxoacid of nitrogen in a reactor,
   ii) feeding at least one of an alkylmercaptan containing stream, a dialkydisulfide containing stream, and a dialkylpolysulfide containing stream into the oxoacid of nitrogen in the reactor to give an alkanesulfonic acid containing product mixture, and
   iii) repeating step ii) until an available inner volume of the reactor is filled completely with the alkanesulfonic acid containing product mixture obtained in step ii),
   iv) feeding additional oxoacid of nitrogen into the reactor, when an amount of the oxoacid of nitrogen provided in step i) is not enough to fill the available inner volume of the reactor with the product mixture obtained in step ii),
   v) feeding an oxygen containing fluid stream into the reactor, when the available inner volume of the reactor is completely filled with the product mixture obtained in the step ii) and/or in the step iii),
   vi) removing at least part of the alkanesulfonic acid containing product mixture from the reactor, and
   vii) feeding at least one of the alkylmercaptan containing stream, the dialkydisulfide containing stream, and the dialkylpolysufide containing stream into the reactor to yield a reaction mixture,
   wherein:
   said alkylmercaptan, dialkyldisulfide and/or dialkylpolysulfide is identical with the alkylmercaptan, dialkyldisulfide and/or dialkylpolysulfide of any of the preceding steps; and
   a volume of the the alkylmercaptan containing stream, the dialkyldisulfide containing stream and the dialkylpolysulfide containing stream, fed into the reactor in step vii), equals a volume of the product mixture removed from the reactor in step vi).

2. The process according to claim 1, wherein the start-up phase of the plant is performed in a batch mode or in a semi-continuous mode.

3. The process according to claim 1, wherein the oxoacid of nitrogen is nitric acid and the process further comprises:
   i') providing at least an amount of the nitric acid according to the formula:

$$\text{nitric acid [mol]} > \frac{(\text{available inner volume reactor [l]} * \text{density alkanesulfonic acid}\left[\frac{kg}{l}\right] * 0.01)}{\text{molar weight of nitrogen dioxide}\left[\frac{kg}{mol}\right]}$$

in the reactor,
   ii') feeding at least one of the alkylmercaptan containing stream, the dialkydisulfide containing stream, and the dialkylpolysufide containing stream into the nitric acid of step i') to give the alkanesulfonic acid containing product mixture, and
   iv') after consumption of the nitric acid in step ii'), feeding the oxygen containing fluid stream into the alkanesulfonic acid containing product mixture.

4. The process according to claim 3, further comprising:
   iii') feeding water, further nitric acid, or a mixture thereof, into the reactor until a stirrer of the reactor is immersed in the alkanesulfonic acid containing product mixture.

5. The process according to claim 3, further comprising:
   v') feeding at least one of the alkylmercaptan containing stream, the dialkydisulfide containing stream, and the dialkylpolysulfide containing stream and the oxygen containing fluid stream into the reactor until the available inner volume of the reactor is filled completely with the alkanesulfonic acid containing product mixture.

6. The process according to claim 1, wherein the steps v) to vii) are performed in a continuous mode or in an essentially continuous mode.

7. The process according to claim 1, wherein the oxygen containing fluid stream is fed into the reactor near to or under, a stirrer of the reactor.

8. The process according to claim 1, wherein the alkanesulfonic acid is prepared from at least one of an alkylmercaptan with a $C_1$ to $C_{12}$ alkyl radical, a dialkyldisulfide with a $C_1$ to $C_{12}$ alkyl radical, and a dialkylpolysulfide with a $C_1$ to $C_{12}$ alkyl radical.

* * * * *